US00PP18732P3

(12) United States Plant Patent
Lemon

(10) Patent No.: US PP18,732 P3
(45) Date of Patent: Apr. 15, 2008

(54) *GERANIUM* PLANT NAMED 'MAESTRO LAVENDER BLUE'

(50) Latin Name: *Pelargonium×hortorum*
Varietal Denomination: Maestro Lavender Blue

(75) Inventor: David G. Lemon, Lompoc, CA (US)

(73) Assignee: Oglevee, Ltd., Connellsville, PA (US)

( * ) Notice: Subject to any disclaimer, the term of this patent is extended or adjusted under 35 U.S.C. 154(b) by 0 days.

(21) Appl. No.: 11/395,353

(22) Filed: Mar. 31, 2006

(65) Prior Publication Data

US 2007/0245439 P1 Oct. 18, 2007

(51) Int. Cl.
*A01H 5/00* (2006.01)

(52) U.S. Cl. ..... Plt./329; Plt./324; Plt./325

(58) Field of Classification Search ..... Plt./324, Plt./325, 329
See application file for complete search history.

*Primary Examiner*—Kent Bell
*Assistant Examiner*—S. B. McCormick-Ewoldt
(74) *Attorney, Agent, or Firm*—The Webb Law Firm

(57) ABSTRACT

'Maestro Lavender Blue' is a new variety of *geranium* having a distinct lavender blue color and excellent outdoor performance.

1 Drawing Sheet

Botanical classification: *Pelargonium×hortorum.*
Varietal denomination: 'Maestro Lavender Blue'.

BACKGROUND OF THE INVENTION

The present invention comprises a new and distinct cultivar of *Pelargonium×hortorum* known by the varietal name 'Maestro Lavender Blue'. The new variety was discovered in Lompoc, Calif. The new variety is a result of cross breeding, 'Designer Lilac Chiffon' (female parent) (U.S. Plant Pat. No. PP9,552) and Seedling Purple 6532 (male parent) (unpatented). The purpose of the breeding program was to develop a more compact series of green leaved zonal *geraniums*. The new variety is similar to flower color to its female parent, but is a more dwarf plant type. The new variety is similar in plant type to its male parent, but exhibits a different, less purple, more lavender flower color than its male parent. 'Maestro Lavender Blue' has a distinct lavender blue color and is a medium size plant with excellent outdoor performance when compared to other varieties known to the breeder. Further, the new variety is similar in plant height and type to 'Tango Lavender' (unpatented), but has a deep flower color and leaves that are lighter green in color. The new variety was first asexually reproduced by cuttings in Connellsville, Pa.

The new variety was grown in a glass greenhouse in Connellsville, Pa. in a 4-inch pot under full light, at 60° F. in the evenings and 68° F. in the daytime in a soilless media with constant fertilizer at 200–250 ppm nitrogen and potassium. The new variety exhibits developed roots at 21 days at an average temperature of 21° C. and has a response time of six to seven weeks from a rooted cutting.

DESCRIPTION OF THE DRAWING

The accompanying photographic drawing illustrates the new variety, with the color being as nearly true as is possible with color illustrations of this type.

DESCRIPTION OF THE PLANT

Figure 1:
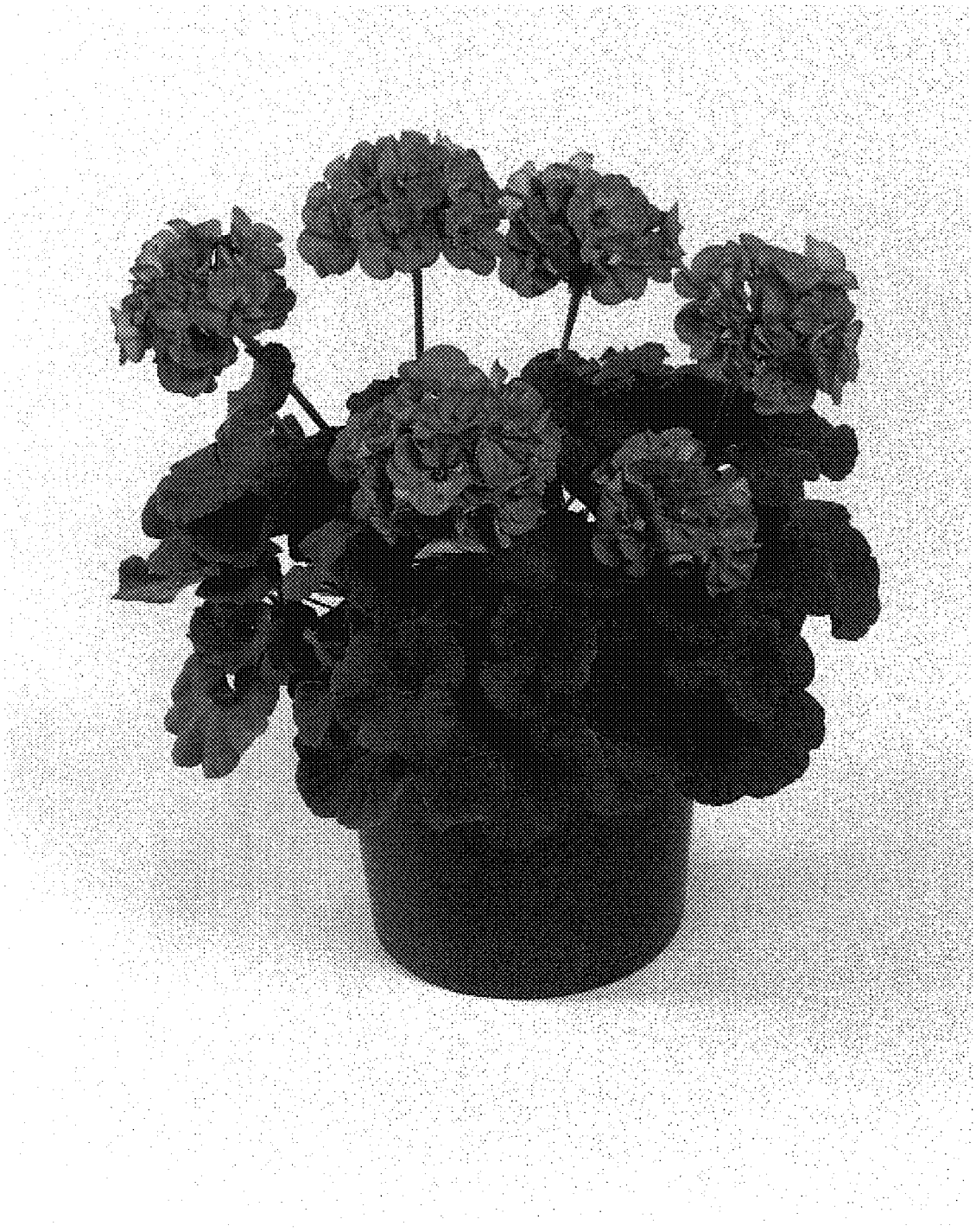

The following detailed description sets forth the characteristics of the new cultivar. The data which defines these characteristics were collected by asexual reproductions carried out in Connellsville, Pa. The color readings were taken indoors under 200–220 foot candles of cool white fluorescent light. The new variety was six weeks from a rooted cutting when described. Color references are primarily to the 1996 R.H.S. Colour Chart of The Royal Horticultural Society of London.

PLANT

Market class: Zonal.
Time to initiate roots: Approximately 7–10 days at about 23° C.
Time to develop roots: Approximately 21 days at about 21° C.
Time to produce a finished flowering plant from a rooted cutting: About 6–7 weeks.
Rooting habit: Good.
Form (e.g., spreading, mounded, symmetrical): Round-mounded.
Height from media surface to top of foliage: 14–16 cm.
Height from media surface to top of flowers: 20–26 cm.
Plant diameter: 23–27 cm.
Vigor: Medium.
Strength: No artificial support needed.
Branching habit: Free branching.
Stem:
- *Main stem length.*—12.5–14.5 cm.
- *Diameter.*—0.7–0.9 cm.
- *Color.*—Yellow-Green Group 144A.
- *Texture.*—Smooth.
- *Pubescence.*—Average.
- *Internode length.*—2.0–3.5 cm.

Lateral branches:
- *Length.*—Primary: 2.0–6.0 cm. Secondary: None at 6 weeks.

*Diameter.*—Primary: 0.5–0.6 cm. Secondary: None at 6 weeks.
*Internode length.*—1.5–2.0 cm.
*Texture.*—Smooth.
*Pubescence.*—Average (moderate).
*Color.*—Yellow-Green Group 144A.

Foliage:
*Stipules.*—Size: 1.0×1.0 to 1.0×1.2 cm. Color: Yellow-Green Group 144A.
*Zonation pattern.*—None present.
*Size of leaf.*—Length: 6.3–10.3 cm. Width: 7.1–11.2 cm.
*Shape of leaf (generally).*—Reniform with a stalked base.
*Shape of apex.*—Rounded in accordance with a reinform leaf shape.
*Shape of base.*—Cordate.
*Texture.*—Velvety.
*Aspect.*—Leaves have a very slight slope increasing from the point of connection toward the margin.
*Margin type.*—Crenate.
*Pubescence.*—Upper surface: Moderate. Lower surface: Moderate.
*Color.*—Young leaves: Upper surface: Green Group 137B. Lower surface: Green Group 138B. Mature leaves: Upper surface: Green Group 137A. Lower surface: Green Group 137C.
*Petiole.*—Length: 5.3–14.3 cm. Diameter: 0.25–0.3 cm. Color: Yellow-Green Group 144A.
*Veins.*—Venation type: Palmate. Color: Upper surface: Green Group 137C. Lower surface: Yellow-Green Group 145B.

INFLORESCENCE

Bud:
*Stage of development when bud characteristics determined.*—Bud shows color at side but sepals are not parting at the tips.
*Shape of cluster.*—Elliptical.
*Diameter of cluster.*—3.7–4.2 cm.
*Number of buds per cluster.*—23–26.
*Shape of individual bud.*—Ellipse.
*Length of individual bud.*—0.8–0.9 cm.
*Width of individual bud.*—0.5–0.7 cm.

Natural flowering season at specified location(s): Year-round horticultural greenhouse crop.
Blooming habit: Continuous and free-flowering.
Umbel diameter of a mature flower.—11.3–12.8 cm.
Umbel depth: 6.2–9.4 cm.
Borne: Umbel, flowers on pedicel, pedicel on peduncle.
Number of inflorescences per lateral branch: 1–2.
Lastingness of an individual flower: 14–21 days from 1$^{st}$ floret.

Florets:
*Form.*—Flat (as the plant matures, the florets gradually more open/flat) and slightly cupped.
*Number per umbel.*—21–32.
*Diameter.*—4.2–5.1 cm.
*Depth.*—2.2–2.6 cm.

Petals:
*Color.*—The top two or three petals of the floret have a white blotch in comparison to the bottom petals.

Upper surface: The top two or three petals have an outer line on the margin of Red-Purple Group 71D. The petals are Red-Purple Group 72C. The bottom half of the petals have a blotch of Red-Purple Group 65C and White Group 155D. The venation below the blotch is Red-Purple Group 71B. Above the blotch the venation fades to a Red-Purple Group 71D. The point of connection fades to White Group 155D. The bottom petals are Red-Purple Group 71D. The point of connection immediately fades to White Group 155D. The venation present is Red-Purple Group 71C.

Lower surface: The top two or three petals have a Red-Purple Group 71D margin and fade to Red-Purple Group 73C and finally to White Group 155D at the center of the petal. The venation present is Red-Purple Group 67A. The point of connection is White Group 155D. The bottom petals are Red-Purple Group 73A on the margin and fade to White Group 155D. The petals have a light venation of Red-Purple Group 67B.

*Shape.*—Inverted teardrop.
*Length.*—2.4–2.7 cm.
*Width.*—1.9–2.6 cm.
*Apex shape.*—Smooth and rounded.
*Base shape.*—Tapered to a point.
*Margin.*—Entire, smooth.
*Number per floret.*—5–8.
*Texture.*—Smooth.
*Tonality from a distance.*—Bright lavender pink flowers atop of mounding medium-dark green foliage.

Petaloids:
*Quantity.*—0–4 per floret.
*Shape.*—Splits in a two-pronged unit or are tubular.
*Color (Upper and lower surface).*—Petaloids have an inner and outer surface of Red-Purple Group 67B and fade to White Group 155D near the point where they connect to the pedicel. The undersides are Red-Purple Group 73A and fade to White Group 155D approaching the center of the petaloid.
*Length.*—1.1–1.5 cm.
*Width.*—0.2–0.9 cm.
*Apex.*—Forked, folded or tubular.
*Base.*—Tapered to a point (like petals).
*Margin.*—Entire.

Pedicel:
*Length.*—3.1–3.6 cm.
*Diameter.*—0.15–0.2 cm.
*Color.*—Greyed-Purple Group 185A where the pedicel connects to the floret and fades to Yellow-Green Group 144A as the pedicel approaches the point where it connects to the peduncle.

Peduncle:
*Length.*—16.8–25.5 cm.
*Diameter.*—0.3–0.5 cm.
*Texture.*—Slightly rough leather texture with a slight to moderate amount of pubescence.
*Color.*—Yellow-Green Group 144A.

Fragrance: Typical.
Disease resistance: None observed to date.
Temperature tolerance: None observed to date.
Drought tolerance: None observed to date.
Fruits/Seeds: None observed to date.

REPRODUCTIVE ORGANS

Stamens:
*Number (per flower).*—8.
*Filament.*—Length: 0.8–0.9 cm. Color: White Group 155D with the tip being Red-Purple Group 66A.
*Anthers.*—Shape: Oval-like with a slight curve. Length: 0.15–0.2 cm. Color: Greyed-Purple Group 185B.
*Pollen.*—Color: Greyed-Orange Group 171B. Amount (generally): Plentiful.

Pistils:

*Number.*—One.

*Length.*—1.0 cm.

*Style.*—Length: 0.3 cm. Color: Red Group 46A.

*Stigma.*—Shape: Style splits and radiates into 5 or 6 parts. Color: Red Group 46A. Size: 0.15 cm high.

*Ovaries.*—Position: Superior. Pubescence: Present. Length: 0.55 mm. Width: 0.17–0.2 cm. Color: Yellow-Green Group 144A.

I claim:

1. A new and distinct variety of *geranium* plant having a distinct lavender blue color and excellent outdoor performance as herein described and illustrated named 'Maestro Lavender Blue'.

* * * * *